United States Patent [19]

Husain et al.

[11] Patent Number: 5,391,459
[45] Date of Patent: Feb. 21, 1995

[54] BIS UREIDO COMPOSITIONS

[75] Inventors: Syeda Husain, Middletown; Allan P. Piechowski, Califon; John F. Pilot, Carteret, all of N.J.

[73] Assignee: Sun Chemical Corporation, Fort Lee, N.J.

[21] Appl. No.: 264,826

[22] Filed: Jun. 23, 1994

Related U.S. Application Data

[62] Division of Ser. No. 118,556, Sep. 9, 1993, Pat. No. 5,380,942.

[51] Int. Cl.$^6$ .............................................. G03C 1/06
[52] U.S. Cl. .................................. 430/264; 430/598; 430/599; 564/59
[58] Field of Search ................... 430/264, 598, 599; 564/59

[56] References Cited

U.S. PATENT DOCUMENTS

| | | | |
|---|---|---|---|
| 4,110,309 | 8/1978 | Schulze et al. | 528/119 |
| 4,115,446 | 9/1978 | Schulze | 260/553 |
| 4,154,724 | 5/1979 | Schulze | 528/68 |
| 4,269,929 | 5/1981 | Nothnagle | 430/264 |
| 4,914,003 | 4/1990 | Yagihara et al. | 430/264 |
| 4,975,354 | 12/1990 | Machonkin et al. | 430/264 |
| 4,988,604 | 1/1991 | Machonkin et al. | 430/264 |
| 5,104,769 | 4/1992 | Looker et al. | 430/264 |
| 5,139,921 | 8/1992 | Takagi et al. | 430/264 |

*Primary Examiner*—Thomas R. Neville
*Attorney, Agent, or Firm*—Jack Matalon

[57] ABSTRACT

Novel compounds have been discovered that are particularly effective as nucleation accelerators or boosters when employed with hydrazide nucleators in the formulation of silver halide emulsions for lithographic film. The novel compounds contain bis ureido groups joined by an alkyleneoxy moiety or recurring alkyleneoxy moieties. The 2-nitrogen of each ureido group can carry groups comprising hydrogen, aryl, alkyl or dialkylaminoalkyl, alike or different.

20 Claims, No Drawings

BIS UREIDO COMPOSITIONS

This is a divisional of application Ser. No. 08/118,556, filed on Sep. 9, 1993, U.S. Pat. No. 5,380,942.

FIELD OF THE INVENTION

This invention relates to novel compositions useful as high contrast boosters or accelerators used in combination with hydrazide nucleators in lithographic films. The invention specifically relates to novel boosters comprising bis ureido alkyleneoxy compositions used in conjunction with high contrast promoting hydrazide nucleators and to the emulsions and film articles containing the novel boosters. The invention also relates to the process for producing the emulsions and film articles containing the novel boosters.

BACKGROUND OF THE INVENTION

It has long been a major challenge to artisans engaged in the formulation of photographic emulsions for lithographic film to find improved emulsion formulations, film articles and/or methods of development that would yield an increasingly sharp reproduction of an image showing superior qualities of contrast. The relatively recent advent of rapid access developers has intensified this challenge to the artisan since some aspects of the chemistry of these newer developers tend to work against the development of high contrast images.

According to the prior art, to obtain high contrast in lithographic films, it necessary to use a high chloride lith emulsion to prepare a film and process the exposed film in a hydroquinone-only developer containing low sulfite. This type of developer had low capacity and was prone to serious degradation of key properties due to aerial oxidation over as little as 1–3 days. The aldehyde bisulfite used to produce the low sulfite concentration also interfered with the hydroquinone using erratic, even non-reproducible development activity. This high contrast "lith effect" (infectious development) was described as early as 1945 in J. Frank. Inst. 239, 221 (1945).

Some initial contrast-enhancing improvements in the art were taught by Trivelli and Smith in U.S. Pat. No. 2,419,975 who noted an increase in speed and contrast by developing in the presence of hydrazine compounds. However, sulfite necessary as an antioxidant in the developer tended to lessen this "hydrazide" effect. Also, many of their hydrazines were used in large quantities and were highly toxic besides being somewhat nonspecific fogging agents that tended to produce high fog in unexposed areas.

Nothnagle, as taught in U.S. Pat. No.4,269,929, improved the hydrazide effect for contrast enhancement by using hydrazines (nucleators) in conjunction with a hydroquinone (H2Q) plus phenidone developer that could contain a high level of sulfite ($SO_3^-$) to prevent aerial oxidation. By further incorporating an amine compound in the developer, a high capacity, stable, long life developer/film system that gave excellent high contrast and speeds was provided. However, it was found that the amino compound frequently was toxic, volatile, odor producing, azeotrope forming, insoluble in the developer and costly and required a pH of 11.5+. Also, higher pH developers tended to oxidize and deplete more quickly with respect to the H2Q contained within them. This leads to contrast, dot quality, speed and pepper problems and inconsistencies. The toxicity of the hydrazides (nucleators) was of minor concern here since they were incorporated into the emulsion.

In Japanese Patent Pub 140340/85, a method to overcome the problems of the amino compound in the developer was described by incorporation of these compounds into the film layer. However, in Japanese Patent Pub 222241/87, problems with incorporating amino ("boosters") compounds were identified that related to their propensity to leach into the developer from the film and cause pepper fog.

Ideally, a high contrast system using a nucleator which works in concert with a booster should have enhanced speeds and gradients with low/no pepper and excellent dot quality, and developable in a non-toxic, non-corrosive stable developer at as low a pH as is practically feasible. Prior art boosters fail many of these goals, are difficult to synthesize, costly and require large concentrations to be effective.

Many of these booster problems are overcome in the prior art by incorporating the booster into the film rather than in the developer. Machonkin, et al., in U.S. Pat. No. 4,975,354, mentions the use of hydrazide compounds, particularly sulfonamide hydrazides with an amino booster that has at least one secondary or tertiary amino group, contains within its structure at least 3 repeating ethyleneoxy units and has a partition coefficient of at least one. However, even these boosters show speed and gradient as well as dot quality variations from sample to sample. These variations are apparent in the examples where the same element compositions are developed under different development conditions. Also, the high molecular weight of some of the compounds requires a large volume of non-aqueous solvent to be included in the emulsion formulation so that the required concentration of booster is soluble in the emulsion. It is not usually desirable to add high volumes of non-aqueous solvent since it can be toxic and can have a deleterious effect on the sensitometric and other properties of the film.

In U.S. Pat. No. 5,139,921 to Takagi, et al., a process is taught for forming super high contrast images using a developer with relatively low pH wherein the film contains a hydrazine and a nucleation accelerator, i.e., booster, that includes alkyl substituted urea and thiourea with a nitro-containing heterocyclic group attached.

Machonkin, et al., in U.S. Pat. No. 4,988,604, teaches a high contrast photographic element that incorporates an aryl sulfonamidophenyl hydrazide containing both thio and ethyleneoxy groups.

It is an object of this invention to provide novel high contrast accelerator or booster compounds for use in conjunction with hydrazide nucleators.

It is a further objective of the invention to provide the foregoing compounds that overcome some of the limitations of the nucleator/booster systems described above.

It is yet a further object to produce improved silver halide (AgX) photographic elements or articles and methods for their manufacture that use these novel boosters incorporated into the film along with hydrazine nucleators.

SUMMARY OF THE INVENTION

A group of novel compounds has been discovered that are particularly effective as nucleation accelerators or boosters when employed with hydrazide nucleators in the formulation of silver halide emulsions for lithographic film. The images produced on developed film containing these boosters are significantly improved in high contrast quality over films that do not contain the novel boosters. Structurally, the novel compounds are distinct in that they contain bis ureido groups joined by an alkyleneoxy moiety or recurring alkyleneoxy moieties. The 2-nitrogen of each ureido group can carry one or two groups comprising hydrogen, substituted or unsubstituted alkyl or dialkyl aminoalkyl. The alkyl groups may be alike or different.

Film elements having high contrast qualities are prepared by coating a suitable substrate with the silver 3halide emulsion containing a nucleator and the booster of the invention.

More particularly, the bis ureido composition useful as a contrast enhancing additive in lithographic film emulsions has the structure:

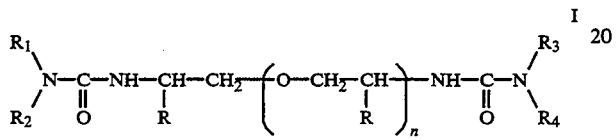

I wherein R is a $C_1$–$C_8$ straight or branched chain alkyl group or hydrogen and n-is at least 3 when R is an alkyl group and at least 1 when R is hydrogen; and $R_1$, $R_2$, $R_3$, and $R_4$ are independently selected from the group consisting of hydrogen, $C_6$–$C_{18}$ aryl groups, $C_1$–$C_8$ straight or branched chain alkyl groups and dialkylaminoalkyl groups having the structure:

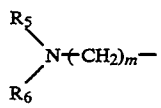

wherein $R_5$ and $R_6$ are the same or different $C_1$–$C_8$ straight or branched chain alkyl groups and m is 2–6. In the foregoing description, the term "aryl" specifically includes phenyl, substituted phenyl and naphthyl.

Particularly preferred compositions of the invention include the following: a) composition I wherein R is hydrogen, n is 2, $R_1$ and $R_3$ are dialkylaminoethyl, $R_2$ and $R_4$ are hydrogen and $R_5$ and $R_6$ are ethyl; b) composition I wherein R is methyl, n is 3, $R_1$ and $R_3$ are hexyl, $R_2$ and $R_4$ are hydrogen and $R_5$ and $R_6$ are ethyl; c) composition I wherein R is methyl, n is 3, $R_1$ and $R_3$ are dialkylaminoethyl, $R_2$ and $R_4$ are hydrogen and $R_5$ and $R_6$ are ethyl.

The invention further comprises a lithographic film article having high contrast qualities and developable in rapid access developers. The article comprises a film substrate having coated thereon a silver halide emulsion containing at least one hydrazine nucleating agent and the bis ureido composition I in an amount sufficient to improve the contrast enhancing qualities of the nucleating agent; typically, the molar ratio of nucleating agent to the bis ureido composition will be in the range of 100:1 to 0.1:1.

The process for forming a high contrast photographic image comprises image-wise exposing a film article comprising a film substrate having coated thereon a silver halide emulsion containing at least one hydrazine nucleating agent and the bis ureido composition I in an amount sufficient to improve the contrast enhancing qualities of the nucleating agent and developing the image-wise exposed film article in a rapid access film developer.

DETAILED DESCRIPTION OF THE INVENTION

The novel booster compounds of the present invention are those bis ureido compounds having the general structure:

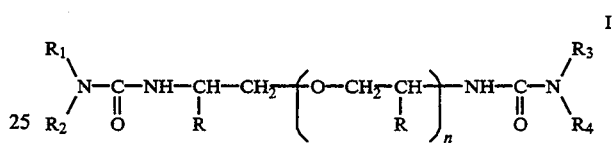

I wherein R is a $C_1$–$C_8$ straight or branched chain alkyl group or hydrogen and n is at least 3 when R is an alkyl group and n is at least 1, preferably 2–13, most preferably 2–3 when R is hydrogen; and $R_1$, $R_2$, $R_3$, and $R_4$ are independently selected from the group consisting of hydrogen, $C_6$–$C_{18}$ aryl groups, $C_1$–$C_8$ straight or branched chain alkyl groups and dialkylaminoalkyl groups having the structure:

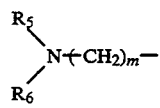

wherein $R_5$ and $R_6$ are the same or different $C_1$–$C_8$ straight or branched chain alkyl groups and m is 2–6. In the foregoing description, the term "aryl" specifically includes phenyl, substituted phenyl and naphthyl.

More specific compounds derived from the general structure I and utilized as boosters in the invention consist of the following:
  a) bis ureido compounds with less than three repeating ethyleneoxy groups linked to adsorption enabling ureido groups having the structure:

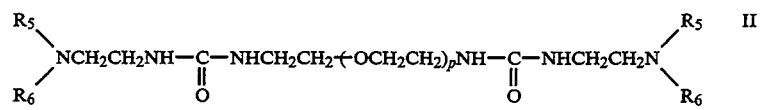

II wherein $R_5$ and $R_6$ are the same or different $C_1$–$C_8$ straight or branched chain alkyl groups, and p is 1–2.

A particularly important compound comprises 1,8-[bis N',N''(diethylaminoethyl)ureido]-3,6-dioxaoctane having the structure:

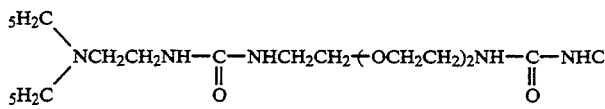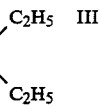 III b) bis N',N" alkyl ureido compounds with z equal to 3 or more repeating propyleneoxy groups linked to adsorption enabling ureido groups; $R_1$ and $R_3$ are hydrogen and $R_2$ and $R_4$ are the same or different $C_1$-$C_8$ straight or branched chain alkyl groups, as shown for compound IV:

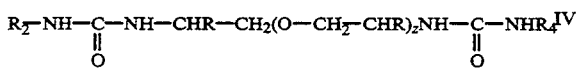 IV

A preferred version of compound IV is that in which z is 3, R is methyl and $R_2$ and $R_4$ are hexyl, i.e. 2,12-bis (N',N"-dihexylureido)-4,7,10-trioxatridecane c) bis ureido compounds having three or more repeating propyleneoxy groups linked to adsorption enabling ureido groups having the structure V:

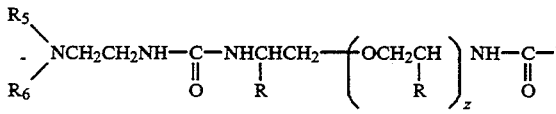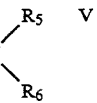 V

The boosters of the present invention provide ureido groups for better adsorption to the silver halide (AgX) surface, lower molecular weights in some cases and good solubility for limiting the amount of methanol added to the emulsion. They work efficiently at lower concentrations and are readily synthesized from available surfactants. They provide high contrast and low pepper when incorporated into the AgX emulsion with hydrazide nucleators. Also, these materials work at the lower pH of 10.8 with typical rapid access developer formulations requiring no special ingredients such as toxic amino alcohols. The booster may be used in a molar ratio of booster to silver halide of 0.0005:1 to 0.01:1, preferably 0.001:1 to 0.005:1.

The following Examples illustrate the application of the novel boosters of the invention.:

Example I

A 100% AgBr emulsion was prepared by controlled double jet (CDJ) precipitation by adding 2N AgNO$_3$ and 2N KBr to a receiver vessel containing 0.05μ AgBr seed crystals, an anti-foaming agent and gelatin for 60 minutes at 60° C. at pAg of 7.0. This produced a monodispersed cubic emulsion with a grain size of 0.25μ. Sodium thiosulfate was added to the emulsion at 250 μm/m AgBr and reacted for 35 minutes at 56° C. to chemically sensitize the crystals. To this emulsion next were added gelatin, KI to yield 0.35 mole % I⁻, spectral sensitizing dyes 3-ethyl-2-(3-(1-ethyl-3-(4-sulfopropyl)-5-(trifluoromethyl)2-benzimidazolinylidenepropenyl)-1-(3-sulfopropyl)-5-trifluoromethyl)benzimidazolium, sodium salt at 63 mg/m AgBr, and 5-chloro-2-(2-((5-chloro-3-(3-sulfopropyl)-2-(3H)-benzoxazolylidene)methyl)-1-propenyl)-3-(3-sulfopropyl)benzoxazolium, triethylamine salt at 92 mg/m, sodium dioctylsulfosuccinate as a coating aid, a polyethylacrylate latex for dimensional stability, a sulfonamido nucleating agent (described in U.S. Pat. No. 5,104,769, col. 5, compound 13, and prepared according to the process described therein in col 5, line 61 et seq.) at 0.4 to 1.9 g/mole AgBr. Also, a booster of the invention, i.e. Compound III, (1,8-[bis N',N"(diethylaminoethyl)ureido]-3,6-dioxaoctane), was added to the emulsion as described above for this Example and Example 2 in the amounts indicated in Tables I and II. These emulsions were then coated on a polyester base with a coating weight of 70 to 75 mg AgBr/dm². An overcoat of gelatin with surfactants and hardening agents was applied over the emulsion layer. The coatings were exposed through a continuous wedge with a tungsten halogen light source for about 6-12 seconds, then developed in a tray with Developer A or Eastman Kodak RA 2000 (commercially available) developer for 30 seconds at 38° C.

The composition of Developer A formulation in g/l, pH 10.95, is as follows:

| | |
|---|---|
| DI water | 670 |
| 45% KOH | 156 |
| DTPA | 15 |
| IRGAFORM ® 3000[1] | 3 |
| Sodium Metabisulfite | 124 |
| Potassium Carbonate | 64 |
| Potassium Bromide | 12 |
| Dimezone-S | 2 |
| Hydroquinone | 58 |
| PMT | 0.05 |
| Benzotriazole | 0.64 |
| 50% Sodium Hydroxide | 46 |
| Boric Acid | 6 |
| Diethylene glycol | 110 |
| Used at: pH = 10.8, 1 + 2 dilution, 30" @ 38° C. | |

[1]Polymaleic acid solution obtainable from CIBA-Geigy Corp.

The results for Example 1 are tabulated in Table I. They show the large boost in line gradient when the booster 1,8-[bis N',N"(diethylaminoethyl)ureido]-3,6-dioxaoctane (Compound III) of the invention is added to the formulation.

TABLE I

| Sample | sulfonamido nucleator | Cpd III | Line gradient[a] | Relative 0.5 speed[b] | B + F |
|---|---|---|---|---|---|
| 1 | 5 × 10⁻³ m/m[c] | 0 | 4.8 | 100 | 0.04 |
| 2 | 5 × 10⁻³ m/m | 5 × 10⁻⁴ m/m | 12.1 | 108 | 0.04 |
| 3 | 5 × 10⁻³ m/m | 5 × 10⁻³ m/m | 24.8 | 113 | 0.04 |

[a]The line gradient is obtained from a measurement of the slope of an H&D curve between 0.5 density and 3.0 density. The H&D curve is a plot of observed densities versus log relative exposure typically from 0 density to 5.0 density on a densitometer.
[b]0.5 speed corresponds to the relative light exposure required to produce a density of 0.5 above base plus fog. For negative films, larger numbers indicate faster films.
[c]m/m = mole/mole of AgX.

A small increase in speed is also seen in Table I as well as no increase in fogging despite the lack of antifogging agent in the emulsion formulation.

Example 2

An 80% chloride AgClBr emulsion was prepared by a simple balanced double jet (BDJ) addition of AgNO₃ and NH₄Cl with KBr, ethylene diamine, NaCl and $RhCl_6^{-3}$ to a water-gelatin ethylene diamine solution for 15 minutes at 35° C. After a 15 minute ripening period, the emulsion was washed and redispersed. Sodium thiosulfate (hypo) was added at 34 μm/m and reacted for 55 minutes at 50° C.; two minutes after the hypo addition, merocyanine dye, 5-[(3-ethyl-2-thioazolidinylidene)ethylidene]-4-oxo-2-thioxo-3-thiazolidene acetic acid, was added at $3.9 \times 10^{-4}$ m/m. These two additions chemically and spectrally sensitize the crystals. After 55 minutes, there added a tetrazaindene stabilizer, iodide at 0.25 mole %, Hcl for chloride adjustment and sulfuric acid for pH adjustment to 5.2. Gelatin was added next followed by sodium dioctylsulfosuccinate and a polyethylacrylate for dimensional stability. The further additions of sulfonamido nucleator of Example 1 with Compound III, 1,8-[bis N',N''(diethylaminoethyl)ureido]-3,6-dioxaoctane, are listed in Table II. These emulsions were then coated on a polyester base with a coating weight of 70 to 75 mg AgBr/dm². An overcoat of gelatin with surfactants and hardening agents was applied over the emulsion layer. The coatings were exposed through a continuous wedge with a tungsten halogen light source for about 6 seconds, and developed in a tray with Developer A at 38° C. for 30 seconds.

Table II shows that the line gradient of the emulsion with nucleator alone is significantly improved as Compound III is added.

TABLE II

| Sample | sulfonamido nucleator | Cpd III | Line gradient | Relative 0.5 speed | B + F |
|---|---|---|---|---|---|
| 4 | $2.5 \times 10^{-3}$ m/m | 0 | 8.4 | 100 | 03 |
| 5 | $2.5 \times 10^{-3}$ m/m | $5 \times 10^{-4}$ m/m | 9.6 | 112 | 03 |
| 6 | $2.5 \times 10^{-3}$ m/m | $1 \times 10^{-3}$ m/m | 12.2 | 115 | 03 |
| 7 | $2.5 \times 10^{-3}$ m/m | $5 \times 10^{-3}$ m/m | 17.3 | 129 | 04 |

Example 3

An emulsion identical to Example 1 was used to test the booster activity of Compound IV, (2,12-bis(N',N''-dihexyl-ureido)-4,7,10-trioxatridecane), with the sulfonamido nucleator of Example 1. The results are summarized in Table III.

TABLE III

| Sample | sulfonamido nucleator | Cpd IV m/m | Dev. | Line gradient | Relative 0.5 speed | B + F |
|---|---|---|---|---|---|---|
| 8 | $2.5 \times 10^{-3}$ m/m | 0 | A | 8.4 | 100 | 04 |
| 9 | $2.5 \times 10^{-3}$ m/m | $7.5 \times 10^{-4}$ | A | 9.8 | 136 | 05 |
| 10 | $2.5 \times 10^{-3}$ m/m | 0 | RA2000 | 5.4 | 100 | 04 |
| 11 | $2.5 \times 10^{-3}$ m/m | $7.5 \times 10^{-4}$ | RA2000 | 9.4 | 131 | 05 |

Here, the addition of booster Compound IV at a low concentration of only $7.5 \times 10^{-4}$ m/m AgBr shows almost a 100% boost in line gradient accompanied by a 30% increase in speed. Most commercially used boosters seem to require a minimum concentration of $1.0 \times 10^{-3}$ m/m for gradient +/or speed boosting.

Example 4

An emulsion identical to Example 2 was used to test the booster activity of Compound V, 2,12-[bis N',N''(diethylaminoethyl)ureido]-4,7,10-trioxatridecane, with the sulfonamido nucleator of Example 1. Developer A was used at a pH of 10.6. The results are summarized in Table IV.

TABLE IV

| Sample | sulfonamido nucleator | Cpd V m/m | Dev. | Line gradient | Relative 0.5 speed | B + F |
|---|---|---|---|---|---|---|
| 12 | $2.5 \times 10^{-3}$ m/m | 0 | A | 9.7 | 100 | 09 |
| 13 | $2.5 \times 10^{-3}$ m/m | $5.0 \times 10^{-4}$ | A | 11.8 | 105 | 09 |

It can be seen that the addition of the booster Compound V at a low concentration of only $5.0 \times 10^{-4}$ m/m shows a 22% boost in line gradient accompanied by a small 5% boost in speed. Again, no increase in fog is seen.

The composition of the invention can be used with the 1-[(alkylbenzenesulfonamido)phenyl]-2-formylhydrazide nucleators described in U.S. Pat. No. 5,104,769, incorporated herein by reference. However, the composition of the invention can also be used with a wide variety of nucleators and is not limited to use with only sulfonamido hydrazide nucleators. Many families of hydrazine or hydrazide nucleators are known to those skilled in the art. The hydrazine compounds used in the emulsions of the invention include those represented by the following general formula, as described by way of example in U.S. Pat. No. 4,323,643: R—Ph—NHNH—CHO wherein R is hydrogen, or an alkoxy, alkyl, acylamino, phenyl, alkylphenyl, phenoxy, or alkylphenoxy moiety.

Amino-phthalimide hydrazide nucleators are also useful in the emulsions as represented by the following general formula described in U.S. Pat. No. 4,882,261:

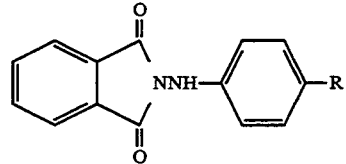

wherein R is hydrogen or alkyl, alkoxy, acylamine, amidoamine or alkylamino.

Other families of hydrazide and hydrazine nucleators useful in the present invention are described in U.S. Pat. Nos. 4,912,016, 4,988,604, 4,994,365, 5,041,355, incorporated herein by reference.

The following Examples present the method by which the specific booster compounds tested in the preceding Examples 1–4 were synthesized. Triethylene glycol diamine, polyoxypropylenediamines, phenyl chloroformate, pyridine and other reagents were obtained from commercial sources. Melting points are uncorrected and were determined on a Unimelt Thomas Hoover melting point apparatus. Infrared spectra were determined on a Beckman Acculab 9 infrared spectrophotometer.

The synthesis was carried out according to the general procedures found in U.S. Pat. No. 4,952,483:

Example 5

Synthesis of Intermediate

Phenyl chloroformate (156.5 g, 1 m) was added dropwise to a stirred solution of triethylene glycol diamine as obtained from Texaco (Jeffamine® EDR 148, 74 g, 0.5 m) and anhydrous pyridine (79 g, 1 m) in acetonitrile (600 ml) at −5° C. After stirring at room temperature for 6 hours, the reaction mixture was poured into excess of ice-water and extracted with methylene chloride. The methylene chloride layer was washed with water, saturated sodium chloride solution and dried over anhydrous magnesium sulfate. Evaporation of solvent on a rotary evaporator gave an oil which on addition of petroleum ether, turned to a solid. Crystallization from methylene chloride and isopropyl ether gave white solid 160 g (82%) with a melting point of 69°–71° C. and infrared nujol ($cm^{-1}$), main bands at 3320, 1700, 1530, 1270, 1205, 1135, 960, 760, 680.

Example 6

Synthesis of Compound III, 1,8-[bis N',N''-(diethylaminoethyl)ureido]-3,6-dioxaoctane The above intermediate (58.2 g, 0.15 m) was dissolved in acetonitrile (250 ml) and after adding N,N-diethylethylenediamine (34.8 g, 0.30 m), the solution was heated at 60°–65° C. for 2 hours. The reaction mixture was then evaporated to a small volume and poured into an excess of water. After extraction with methylene chloride and washing successively with 3–5% cold sodium hydroxide solution, water and sodium chloride solution, the organic layer was dried over anhydrous magnesium sulfate and evaporated on a rotary evaporator. The viscous oil was then heated to 100° C. at 0.01 mm/Hg to remove volatile materials and further dried in vacuo over $P_2O_5$. Yield 35.6 g (55%) infrared (neat) $cm^{-1}$, main bands at 3270, 1640, 1560, 1470, 1380, 1265, 1130.

Example 7

Synthesis of Compound IV, 2,12-bis(N',N''-dihexylureido)-4,7,10-trioxatridecane

A solution of polyoxypropylenediamine, mol wt 230, (Jeffamine D-230®, 9.2 g, 0.04 m) in anhydrous acetonitrile (50 ml) was cooled to −5° C. Hexylisocyanate (10.16 g, 0.08 m) in acetonitrile (20 ml) was added dropwise. The reactants were stirred below 0° C. for 1 hour and warmed to 40°–50° C. for 5 hours. After cooling to room temperature, the clear solution was decanted from a small amount of gum and evaporated on a rotary evaporator. The jellylike material was dissolved in methylene chloride, washed with dilute hydrochloric acid (1%), water, saturated sodium chloride solution, and dried over anhydrous magnesium sulfate. Evaporation of solvent afforded jelly-like material which was heated to 80°–90° C. under vacuum (0.01 mm/Hg) to remove volatile materials. It was further dried in vacuo over $P_2O_5$: Yield 16.5 g (82%); infrared, (neat) $cm^{-1}$, main band 3340, 1630, 1560, 1460, 1370, 1250, 1110, 1030, 930, 770.

Example 8

Synthesis of Compound V, 2,12-[bis N',N''-(diethylaminoethyl)ureido]-4,7,10-trioxatridecane Phenyl chloroformate (9.4 g, 0.06 m) was added dropwise to a stirred solution of polyoxypropylene diamine (Jeffamine® D-400, 12.66 g, 0.0317 m) and anhydrous pyridine (4.74 g, 0.06 m) in acetonitrile (60 ml) at −5° C. After stirring at room temperature for 4 hours, the reaction mixture was poured into an excess of ice water and extracted with methylene chloride. The methylene chloride layer was washed with water, saturated sodium chloride solution and dried over magnesium sulfate. Evaporation of solvent on a rotary evaporator gave a dark viscous oil 20 g, (95%) which could not be distilled. Infrared (neat) $cm^{-1}$ main bands at 3320, 1720, 1590, 1475, 1370-1240, 1200, 1105, 1025, 930, 750.;

The above intermediate (6.62 g, 0.01 m) was dissolved in 45 ml of acetonitrile and after adding N,N-diethylethylene diamine (2.9 g, 0.025 m), the solution was heated at 60°–65° C. for 3–4 hours. The reaction mixture was then cooled to room temperature and poured into an excess of cold water and extracted with methylene chloride and washed successively with 3–5% cold sodium hydroxide solution, water and brine. The organic layer was dried over anhydrous magnesium sulfate and evaporated on a rotary evaporator and finally at 0.01 mm/Hg to remove volatile materials and provide a dark viscous oil. Yield: 6.4 g(90%), infrared (neat) $cm^{-1}$ main bands 3340, 1630, 1550, 1450, 1375, 1250, 1100, 930.

What is claimed is:

1. A lithographic film article comprising a film substrate having coated thereon a silver halide emulsion containing at least one hydrazine nucleating agent and a bis ureido composition having the structure:

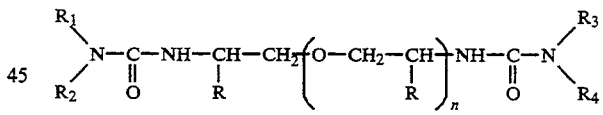

wherein R is a $C_1$–$C_8$ straight or branched chain alkyl group or hydrogen and n is at least 3 when R is an alkyl group and at least 1 when R is hydrogen; and $R_1$, $R_2$, $R_3$, and $R_4$ are independently selected from the group consisting of hydrogen, $C_6$–$C_{18}$ aryl groups, $C_1$–$C_8$ straight or branched chain alkyl groups and dialkylaminoalkyl groups having the structure:

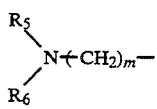

wherein $R_5$ and $R_6$ are the same or different $C_1$–$C_8$ straight or branched chain alkyl groups and m is 2-6.

2. The film article of claim 1 wherein said nucleating agent comprises a 1-[(alkylbenzenesulfonamido)-phenyl]-2-formylhydrazide.

3. The film article of claim 1 wherein said emulsion contains spectral sensitizing dyes.

4. The film article of claim 1 wherein the molar ratio of nucleating agent to bis ureido composition is between 100:1 and 0.1:1.

5. The film article of claim 1 wherein said emulsion contains between $1 \times 10^{-2}$ and $5 \times 10^{-4}$ mole of bis ureido composition per mole of silver halide.

6. The film article of claim 1 wherein said emulation contains a bis ureido composition wherein n is 2 to 13.

7. The film article of claim 1 wherein the bis ureido decomposition comprises 1,8-[bis N',N''(diethylaminoethyl)ureido]-3,6-dioxaoctane having the structure:

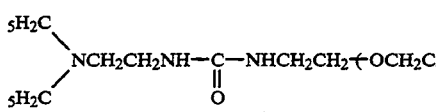

8. The film article of claim 1 wherein the bis ureido composition has the structure:

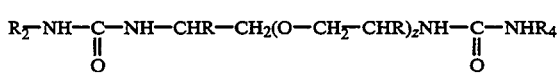

wherein z is equal to at least 3 and $R_2$ and $R_4$ are the same or different $C_1$-$C_8$ straight or branched chain alkyl groups.

9. The film article of claim 8 wherein z is 3, R is methyl and $R_2$ and $R_4$ are each hexyl.

10. The film article of claim 1 wherein the bis ureido composition has the structure:

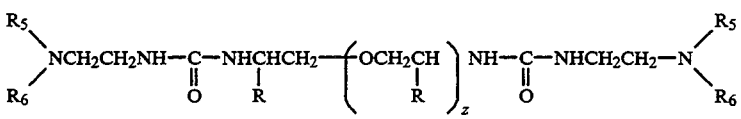

wherein z is equal to at least 3 and $R_5$ and $R_6$ are the same or different $C_1$-$C_8$ straight or branched chain alkyl groups.

11. The film article of claim 10 wherein z is 3, R is methyl and $R_2$ and $R_4$ are each hexyl.

12. The film article of claim 1 wherein the bis ureido composition has the structure:

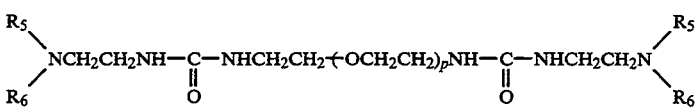

wherein $R_5$ and $R_6$ are the same or different $C_1$-$C_8$ straight or branched chain alkyl groups, and p is 1-2.

13. A process for forming a high contrast photographic image comprising image-wise exposing a film article comprising a film substrate having coated thereon a silver halide emulsion containing at least one hydrazine nucleating agent and a bis ureido composition and developing said exposed film article in a rapid access film developer, wherein said his ureido composition has the structure:

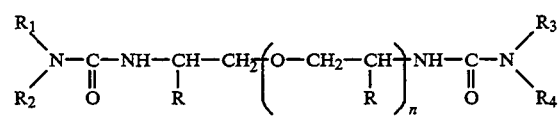

wherein R is a $C_1$-$C_{18}$ straight or branched chain alkyl group or hydrogen and n is at least 3 when R is an alkyl group and at least 1 when R is hydrogen; and $R_1$, $R_2$, $R_3$, and $R_4$ are independently selected from the group consisting of hydrogen, $C_6$-$C_{18}$ aryl groups, $C_1$-$C_8$ straight or branched chain alkyl groups and dialkylaminoalkyl groups having the structure:

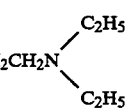

wherein $R_5$ and $R_6$ are the same or different $C_1$-$C_8$ straight or branched chain alkyl groups and m is 2-6.

14. The film article of claim 13 wherein said emulsion contains a bis ureido composition wherein n is 2 to 13.

15. The film article of claim 13 wherein the bis ureido composition comprises 1,8-[bis N',N''(diethylaminoethyl)ureido]-3,6-dioxaoctane having the structure:

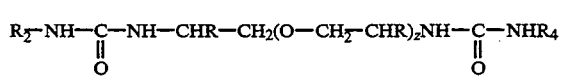

16. The film article of claim 13 wherein the bis ureido composition has the structure:

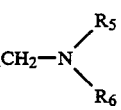

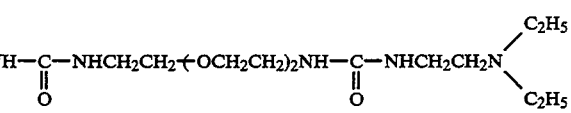

wherein z is equal to at least 3 and $R_2$ and $R_4$ are the same or different $C_1$-$C_8$ straight or branched chain alkyl groups.

17. The film article of claim 16 wherein z is 3, R is methyl and $R_2$ and $R_4$ are each hexyl.

18. The film article of claim 13 wherein said emulsion contains the bis ureido composition of claim 19 wherein z is 3, R is methyl and $R_5$ and $R_6$ are each hexyl.

19. The film article of claim 13 wherein the bis ureido composition has the structure:

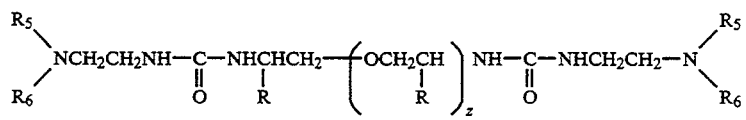

wherein z is equal to at least 3 and $R_5$ and $R_6$ are the same or different $C_1$-$C_8$ straight or branched chain alkyl groups.

20. The film article of claim 13 wherein the bis ureido composition has the structure:

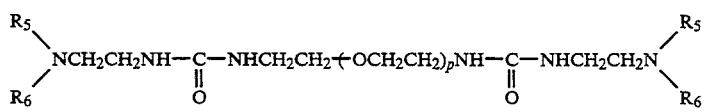

wherein $R_5$ and $R_6$ are the same or different $C_1$-$C_8$ straight or branched chain alkyl groups, and p is 1–2.

* * * * *